United States Patent [19]

Beuchat et al.

[11] Patent Number: 5,224,942
[45] Date of Patent: Jul. 6, 1993

[54] SURGICAL METHOD AND APPARATUS UTILIZING LASER ENERGY FOR REMOVING BODY TISSUE

[75] Inventors: Charles E. Beuchat, Irvine; Scott Rowe, Mission Viejo; Edward G. Malk, Lake Forest; Woodrow W. Watson, Mission Viejo, all of Calif.

[73] Assignee: Alcon Surgical, Inc., Fort Worth, Tex.

[21] Appl. No.: 827,024

[22] Filed: Jan. 27, 1992

[51] Int. Cl.$^5$ .............................................. A61B 17/22
[52] U.S. Cl. ....................................... 606/15; 606/128; 606/4
[58] Field of Search .................................... 606/3-6, 606/10-17, 128

[56] References Cited

U.S. PATENT DOCUMENTS

| | | | |
|---|---|---|---|
| 4,531,934 | 7/1985 | Kossovsky et al. | 606/128 X |
| 4,587,972 | 5/1986 | Morantte, Jr. | 606/15 X |
| 4,605,003 | 8/1986 | Oinuma et al. | 606/128 |
| 4,729,373 | 3/1988 | Peyman | 606/4 |
| 4,932,954 | 6/1990 | Wondrazek et al. | 606/15 X |
| 5,071,422 | 12/1991 | Watson et al. | 606/15 X |
| 5,123,902 | 6/1992 | Müller et al. | 606/6 |

FOREIGN PATENT DOCUMENTS

| | | | |
|---|---|---|---|
| 9110403 | 7/1991 | PCT Int'l Appl. | 606/128 |
| WO91/06271 | 5/1992 | PCT Int'l Appl. | |

OTHER PUBLICATIONS

Effects of Shielded or Unshielded Laser & Electrohydraulic Lithotripsy, Journal of Urology, pp. 857–860, 1990.

R. F. Steinert, et al., *The Nd-YAG Laser in Ophthalmology: Principles and Clinical Applications of Photodisruption*, "Chapter 3: Optical Breakdown, Plasma Formation, and Photodisruption", W. B. Saunders Company, 1985, pp. 22–32.

Primary Examiner—Peter A. Aschenbrenner
Attorney, Agent, or Firm—Sally Yeager; Jeffrey S. Schira; Christopher W. Brody

[57] ABSTRACT

An improved surgical method and apparatus using laser energy for destroying body tissue which includes a surgical handpiece including a surgical tip assembly which is driven by means of laser to achieve optical breakdown, plasma formation and shockwave generation to emulsify or destroy body tissue. The surgical tip assembly includes a laser fiber, a focusing means to enhance optical breakdown of tissue or fluid caused by laser energy transmitted through the laser fiber and an emulsification tip that is resonate tuned to vibrate in response to shockwaves produced by the optical breakdown caused by the laser energy. The emulsification tip and focusing means are configured in a spaced relationship to form an acoustic resonating chamber which further emulsifies body tissue and facilitates mixing of tissue with irrigation fluid.

13 Claims, 2 Drawing Sheets

U.S. Patent  July 6, 1993  5,224,942

SURGICAL METHOD AND APPARATUS UTILIZING LASER ENERGY FOR REMOVING BODY TISSUE

FIELD OF THE INVENTION

The present invention is directed to an improved surgical method and apparatus utilizing laser energy for removing body tissue; and more particularly, to an improved surgical method and apparatus which converts laser energy to acoustical vibrational energy to emulsify body tissue during surgical procedures.

BACKGROUND ART

In the prior art, a plurality of hand-held surgical devices have been proposed which are operable by ultrasonic vibrations to emulsify body tissue. For instance, these devices utilize ultrasonic transducer components which are operable for converting electrical energy to ultrasonic vibrational energy. This vibrating ultrasonic energy is directed to a surgical tip assembly whereby the vibrations are imparted to tissue so as to emulsify the latter. This approach for removing tissue has gained wide-spread acceptance in the surgical field. Devices of this type are described in U.S. Pat. Nos. 3,589,363; 4,223,676; 4,246,902; 4,493,694; and 4,922,902.

In addition, there have been proposed surgical devices which utilize laser energy for removing tissue. One type of laser operated device is a surgical handpiece which is describe in U.S. Pat. No. 4,694,828 to Eichenbaum, wherein a laser beam is directed onto body tissue. The laser beam is effected to vaporize such tissue which is subsequently aspirated from the surgical site.

In the publication entitled "The Nd-YAG Laser in Ophthalmology, Principles and Clinical Applications of Photodisruption", by Steinert et al., the optical breakdown associated with utilization of laser energy is explained. More particularly, optical breakdown is a non-linear effect achieved when laser light is sufficiently condensed in time and space to achieve high irradiance or density of power. During optical breakdown of light energy, an ionized state or plasma is formed. The rapid plasma expansion generates a shockwave which may be followed by cavitation or vapor bubble formation. Collapse of the cavitation or vapor bubbles also contributes to shockwave generation. By focusing laser energy on a target material such as gas, liquid or a solid, damage to the target material may be caused by the sequence of optical breakdown, plasma formation and shockwave generation.

Another type of laser operated surgical device uses a handpiece that carries an optical fiber which delivers laser energy therealong to a surgical tip assembly. In the tip assembly, the laser energy is converted to ultrasonic or acoustical vibrational energy which is then mechanically transmitted by the tip assembly to the tissue that is to be removed. Resulting vibrations emulsify the tissue it contacts. These types of laser operated surgical handpieces are described in U.S. Pat. Nos. 4,729,373 to Peyman and 4,932,954 to wondrazek et al.

In another laser device and as disclosed in U.S. Pat. No. 4,887,600 to watson et al., laser pulses are delivered via an optical fiber to break down stones, calcified tissue or the like. In this device, the distal end of the optical fiber is placed in contact with the material to be broken down.

U.S. Pat. No. 4,608,979 discloses an apparatus which produces focused shockwaves derived from laser energy for the fragmentation of concretions such as kidney stones. In this apparatus, a laser beam is focused in a first position by coupling and focusing means, wherein a shockwave produced by the focused laser beam is then directed to a concretion in a living body.

In systems using laser operated surgical handpieces that transmit laser energy by virtue of an optical fiber through an opening in a tip assembly, clogging of the tip assembly occurs as a result of insufficient emulsification of body tissue which hinders subsequent operation of the handpiece. In addition, prior art techniques that use ultrasonic energy require high amounts of energy which can be transferred to the surgical site and result in surgical complications. In response to these difficulties with prior art devices, a need has developed to provide a surgical method and apparatus for removing body tissue that minimizes potential for surgical complications as well as prevent or minimize system failure by clogging of surgical tip assemblies by partially emulsified body tissue or material.

In response to this need, an improved method and surgical apparatus for removing tissue from surgical sites has been developed which overcome problems associated with prior art devices. The improved surgical apparatus includes a device that uses vibratory motion of a tip driven by means of laser energy optical breakdown to emulsify body tissue. In addition, the device includes irrigating and aspirating means to provide irrigating fluid for emulsification and removal of emulsified material, respectively. The laser energy is transmitted through an optical fiber and focusing means which generate a shockwave to produce vibrational motion in the tip as well as an acoustic resonator which further emulsifies body tissue or material.

Applicants are unaware of any prior art, including the above-listed prior art documents, which teach or suggest a method and surgical apparatus for removing body tissue using laser energy which includes a handpiece comprising a surgical tip assembly that combines laser means for creating optical breakdown and a shockwave to cause vibrations in the tip of the tip assembly and subsequent destruction or emulsification of body tissue.

SUMMARY OF THE INVENTION

It is accordingly an object of the present invention to provide a surgical method and apparatus utilizing laser energy for removing body tissue.

It is a further object of the present invention to provide a surgical apparatus for removing body tissue using laser energy which includes a handpiece assembly, a surgical tip assembly, fiber optic means for transmitting laser energy to the tip assembly, and aspiration/irrigation means for use during surgical techniques.

It is a still further object of the present invention to provide a surgical method and apparatus for removing body tissue from a surgical site which includes the application of vibrations in a tip induced by optical breakdown of laser energy to emulsify body tissue at the surgical tip.

It is a yet further object of the present invention to provide an improved surgical method and apparatus which includes a staged emulsification of body tissue or material which enhances and improves emulsification of body tissue.

It is still a further object of the present invention to provide a surgical method and apparatus utilizing laser energy for removal of body tissue which minimizes emission of laser light and laser heating at the surgical site.

It is another object of the present invention to provide a surgical method and apparatus that is useful in surgical procedures such as cartilage removal, soft tissue removal, plaque removal in arteries and caries removal in dentistry and cataract removal.

In satisfaction of the foregoing objectives and advantages, there is provided a surgical apparatus utilizing laser energy for removing body tissue which includes a handpiece assembly, the handpiece assembly including a surgical tip assembly. The surgical tip assembly includes an aspiration and irrigation cannula and an emulsification tip at the distal end of the tip assembly. Extending through the cannula is a laser fiber which is connected at one end to a source of laser energy and connected at the other end to a focusing means. The focusing means is positioned in a spaced relationship with the emulsification tip and creates a channel for passage of irrigation and aspiration fluids. An acoustic resonator/chamber is formed in the space between the emulsification tip and the focusing means which provides further acoustical energy for tissue emulsification during use of the apparatus.

Also disclosed is a surgical method which includes transmitting laser energy through the laser fiber to the focusing means located within the cannula. The focusing means enhances optical breakdown of the tissue or fluid by the laser energy and directs the shockwave produced thereby towards the emulsification tip to produce a vibration therein. The vibrations transmitted to the emulsification tip emulsify body tissue or material in contact therewith. The emulsified tissue is then channeled through apertures in the emulsification tip into an acoustic resonator/chamber where further emulsification occurs along with introduction of irrigating fluid and aspiration of emulsified tissue.

BRIEF DESCRIPTION OF DRAWINGS

Reference is now made to the drawings accompanying the application wherein.

DESCRIPTION OF THE PREFERRED EMBODIMENTS

The present invention is concerned with surgical apparatus and methods utilizing laser energy to remove body tissue. According to the present invention, it has been discovered that improved emulsification of body tissue can be achieved by utilizing a surgical handpiece assembly which includes a surgical tip assembly having an emulsification tip at the distal end thereof. The surgical tip assembly also includes an aspiration/irrigation cannula which permits irrigation fluid to be supplied to the surgical site as well as aspiration of emulsified tissue therefrom.

The surgical tip assembly includes means for transmitting laser energy to a focusing means which enhances optical breakdown of tissue or fluid by laser energy, the optical breakdown and plasma formation generating a shockwave which is transmitted to the emulsification tip. It should be understood that optical breakdown refers to the process as described above when laser energy strikes a target and forms a plasma. The shockwave vibrates the emulsification tip to emulsify body tissue in contact with the tip. The emulsification tip, the focusing means, the laser fiber, and the irrigation and aspirating means are housed in a hollow tip to prevent laser light from contacting undesired areas of tissue and causing damage thereto. Furthermore, by utilizing laser energy to provide the source of vibratory motion of the emulsifying tip, potential surgical complications due to higher energy levels used in prior art devices such as ultrasonic surgical handpieces are minimized.

The inventive surgical apparatus and method also provide improved emulsification of body tissue by creating an acoustic resonator between the emulsification tip and the laser fiber focusing means which further emulsifies tissue that was not destroyed by the emulsifying tip.

One embodiment of the surgical method and apparatus provides advantages over other prior art devices that utilize laser energy to break down tissue through an opening in the tip of the laser device. In this embodiment, the laser driven surgical apparatus includes a sealed tip assembly which provides a chamber for optical breakdown to occur separate from tissue, fluid or emulsified material. In addition, this embodiment provides improved emulsification by producing cavitation along with the mechanical vibratory cutting motion of the tip of the surgical tip assembly.

Figures 1, 2, 3:
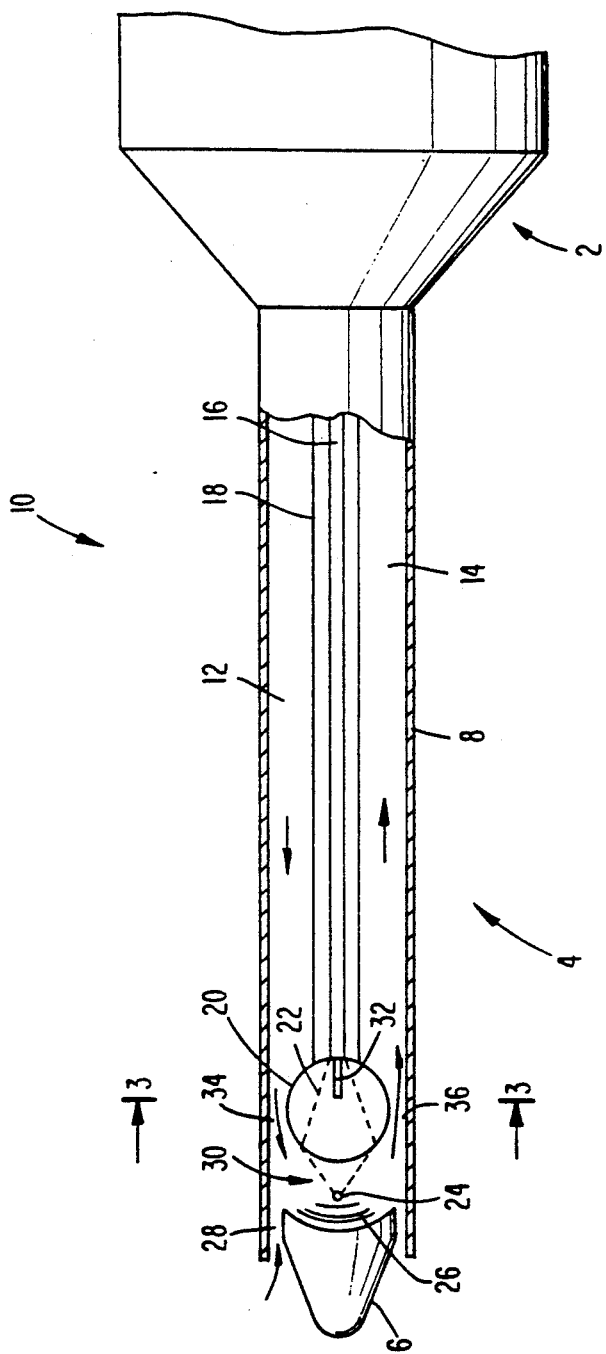
FIG. 1 shows a side view of one embodiment of the surgical apparatus of the present invention including portions broken away to show greater detail in cross-section.
FIG. 2 shows an end view of the embodiment depicted in FIG. 1.
FIG. 3 shows a cross-sectional view along the line III—III of FIG. 1.

With reference to FIG. 1 firstly, one embodiment of the improved surgical apparatus of the present invention is generally designated by reference numeral 10 and is seen to include a handle 2, a surgical tip assembly 4 and an emulsification tip 6. The surgical tip assembly also includes a hollow cannula 8 having an irrigation channel 12 therein along with an aspiration channel 14. The irrigation channel 12 is connected to means for supplying irrigating fluid (not shown) and the aspiration channel 14 is connected to means to aspirated fluid from the tip assembly (not shown). It should be understood that the means to provide irrigation fluid and aspiration are well known in the prior art and are not considered an aspect of the present invention. The means for aspirating may include a vacuum source and the irrigation fluid may be a typical saline solution used in, for example, cataract surgery.

The surgical handpiece assembly 10 also includes a laser fiber 16 extending therethrough, the laser fiber 16 being enclosed by a fiber holder or sheath 18. The fiber holder 18 in the tip assembly 4 provides the necessary rigidity for expectant use of the device. The laser fiber 16 is connected via the handpiece to a laser that will provide a pulsed burst of energy to the surgical tip assembly to achieve optical breakdown of the fluid or tissue and plasma formation within the emulsification tip. Ideally, the laser energy will be provided by a Q-switched, short pulse width, Nd: YAG laser but any known high peak power laser energy source may be utilized with the inventive surgical handpiece. The pulse rate of the laser should be adjustable between 1-40 Hz. and the energy range should be adjustable from between about 0.1 to 20 millijoules. The laser fiber can have a range of diameter between about 200-600 microns with a preferred diameter being 300 microns. The laser fiber may be made out of any known material such as fused silica or the like. The handle in conjunction with the laser energy source and irrigation and aspiration source means may be any type or configuration known in the art and are not considered to be aspects of the present invention.

Still with reference to FIG. 1, the laser fiber 16 has a focusing means, an optical sphere 20 attached at the distal end thereof. The optical sphere 20 may be made out of any lens material such as sapphire, cubic zirconia or silicon. The optical sphere may be attached to the laser fiber in any known manner such as through the use of an adhesive or cement. Alternatively, the optical sphere may be formed as part of the fiber. The optical sphere 20 performs a multifunctional role in the inventive device in that it provides a focusing means to focus the laser light as indicated by the dashed lines 22 to enhance optical breakdown of tissue and/or fluid and plasma formation at the reference numeral 24. The optical breakdown creates a shockwave designated by the reference numeral 26 which causes the emulsification tip 6 to vibrate. The vibratory motion of the emulsification tip emulsifies tissue in direct contact with the tip. Furthermore, cavitation occurs by the tip moving through body fluid to further enhance emulsification of body tissue.

With reference to FIG. 2 and FIG. 1 again, the emulsification tip 6 is a resonate tuned type emulsification tip which has a natural resonating frequency set to the acoustic shockwave driven frequency produced by the optical breakdown process. In this manner, the tip vibrates in response to the shockwave generated by the optical breakdown process. The emulsification tip 6 has an opening 3 therethrough and a conic configuration that creates a plurality of emulsification/entry ports 28 between the tip 6 and the hollow cannula 8. The entry ports 3 and 28 provide further emulsification of tissue by mechanical, vibrational and acoustic energy as well as a channel for funneling emulsified body tissue to the acoustic resonate/chamber 30 formed in the space between the emulsification tip 6 and the optical sphere 20. The emulsification tip may be made out of any material that is capable of receiving the shockwaves produced by the optical breakdown and converting the shockwaves to vibrational energy. A preferred material would include titanium.

The acoustic resonator/chamber 30 provides final emulsification of body tissue as well as mixing of body tissue with irrigant supplied from irrigation channel 12. Body tissue located in the acoustic resonate/chamber 30 may be aspirated via aspiration channel 14 and a source of aspiration (not shown).

The optical sphere 20 acts as one half of the acoustic resonator/chamber as well as a means for creating a venturi effect which regulates the irrigation fluid and guides the circulation of irrigation/aspiration fluidics. As can be seen from FIG. 3, the cannula 8 includes fluidic vanes 32 which create an upper irrigation channel 34 and a lower aspiration channel 36. The reduction in area of channels 34 and 36 when compared to irrigation channel 12 and aspiration channel 14, respectively, creates a venturi effect to enhance flow of irrigation fluid as well as aspiration of emulsified material. It should be understood that the fluidic vanes 32 extend along the length of the cannula 8 to provide the dual channels necessary for irrigation and aspiration.

Figure 4:
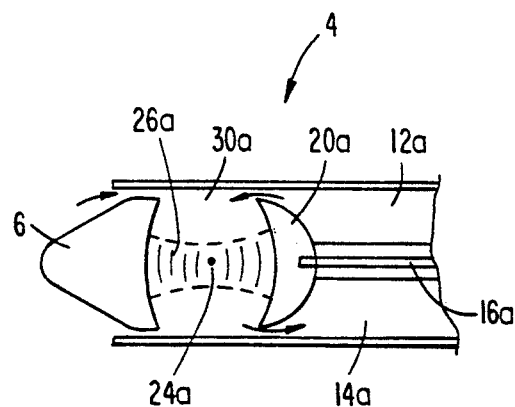
FIG. 4 shows a further embodiment of the inventive surgical apparatus.

In a further embodiment, and with reference to FIG. 4, a surgical tip assembly is generally designated by the reference numeral 4a and is seen to include a meniscus-type lens focusing means 20a. In this configuration, the laser energy is focused at the reference numeral 24a and a more stable shockwave 26a is created than the shockwave illustrated in the embodiment of FIG. 1.

Figure 5:
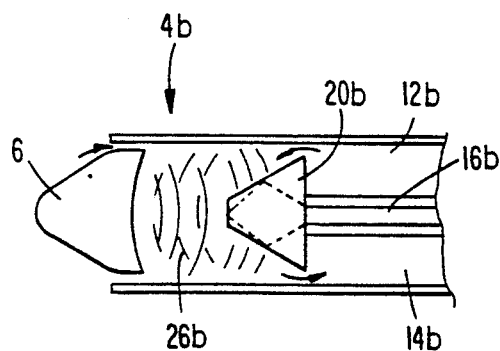
FIG. 5 shows another embodiment of the surgical apparatus of the present invention.

FIG. 5 shows a still further embodiment of the inventive device and is seen to include a surgical tip assembly 4b which includes a conical focusing means 20b. In this configuration, an unstable acoustic resonator/chamber 26b is created, similar to the acoustic resonator/chamber depicted in the embodiment illustrated in FIG. 1.

With reference back to FIG. 1, it should be understood that the emulsification tip 6 is removable from the hollow cannula 8. Furthermore, the hollow cannula 8 is also removable from the handle 2. The handle 2 is adapted to be held by a surgeon for facilitating surgical procedures such as caries removal in dentistry, plaque removal in arteries, cataract surgery, cartilage removal for orthopedic surgery and soft tissue removal. Alternatively, the surgical tip assembly may be attached to a handle or other holder which can be manipulated mechanically rather than by hand.

In an exemplary method of removing body tissue, and with reference back to FIG. 1 again, a pulse of 1064 nanometer laser light energy is transmitted down the fiber 16 towards the optical sphere 20. The sphere 20 first acts as a lens, focusing the optical energy to a point 24 with sufficient irradiance and fluence to achieve optical breakdown of tissue or fluid. Once optical breakdown is achieved, acoustic energy via the shockwave front produced by the optical breakdown is coupled into the emulsification tip 6. The emulsification tip is driven to a natural resonating frequency of oscillation by the acoustic frequencies generated by the optical breakdown process. As the emulsification tip comes into contact with body tissue to be removed, emulsification takes place and the body tissue is drawn through the entry ports 28 into the acoustic resonator/chamber 30. By virtue of the lower pressure in the acoustic resonator/chamber 30, the emulsified body tissue adjacent the tip 6 is drawn therein. By creating an unstable acoustic resonator/chamber between the emulsification tip 6 and the optical sphere 20, further emulsification occurs within the chamber 30. At the same time that further emulsification is occurring in the chamber 30, irrigation fluid is being supplied through the irrigation channel 34 and over the surface of the optical sphere 20. At the same time, aspiration suction is provided via the aspiration channel 34 to clear the chamber 30 of material that has been emulsified. Providing the irrigation fluids as well as aspiration suction promotes mixing and circulation of fluids within the chamber 30. It should be understood that the irrigating and aspirating functions may be alternated to first irrigate and subsequent thereto aspirate in another mode of operation. In addition, the flow of irrigation fluid as well as the level of aspiration suction can be adjusted during surgery to compensate for the body tissue emulsified and ingested into the surgical tip assembly.

In addition, the laser energy transmitted through the laser fiber as well as the optical sphere diameter and index of refraction thereof can be chosen to give flexibility in locating the optical breakdown point in the resonator, thus "seeding" the resonator for optimal propagational effects.

Figure 6:
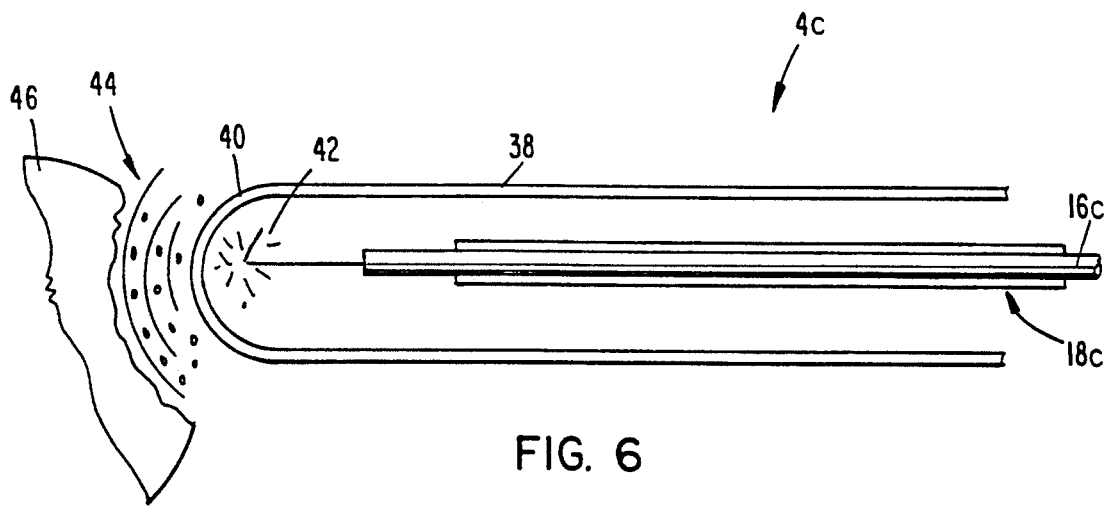
FIG. 6 shows still another embodiment of the improved surgical apparatus of the present invention.

In an additional embodiment and with reference to FIG. 6, a surgical tip assembly 4c is illustrated and is seen to include a laser fiber 16 enclosed in a sealed tube assembly 38. The sealed assembly 38 includes a rounded distal end 40 which is designed to contact body tissue 46. In use, laser energy is transmitted to the laser fiber 16 and produces optical breakdown in the area designated by the reference numeral 42. The optical breakdown and plasma formation in the gas within the tube 38 generates a shockwave which is transmitted to the tip 40. The vibratory motion of tip 40 emulsifies the body tissue 46 in the area 44 and produces cavitation which further enhances the emulsification process. In this embodiment, the sealed tube 38 has sealed end 40 thereon. This embodiment prevents obstruction or clogging of the tip assembly and permits optical breakdown to occur in a gas rather than a liquid, solid or mixture thereof as described above. Of course, the surgical tip assembly 4c may be combined with irrigation and aspiration means, laser energy means and a handpiece as are well known in the prior art.

As such, an invention has been disclosed in terms of preferred embodiments thereof which fulfill each and every one of the objects of the present invention as set forth hereinabove and provides a new and improved surgical apparatus and method utilizing laser energy to remove body tissue.

Of course, various changes, modifications and alterations in the teachings of the present invention may be contemplated by those skilled in the art without departing from the intend spirit and scope thereof. As such, it is intended that the present invention only be limited by the terms of the appended claims.

We claim:

1. An apparatus for emulsifying body tissue during surgery comprising means for providing laser energy to a surgical tip assembly, said surgical tip assembly further comprising:
   i) first means for transmitting said laser energy along said surgical tip assembly to achieve optical breakdown and plasma formation in a material to generate acoustic vibrational energy, said first means axially aligned with an axis of said surgical tip assembly; and
   ii) second means for transmitting said acoustical vibrational energy to said body tissue for initial emulsification thereof, wherein said first means for transitting said laser energy is spaced from and axially aligned with said second means for transmitting said acoustical vibrational energy to form an acoustic resonating chamber axially aligned therebetween to further emulsify body tissue initially emulsified by said second means for transitting acoustical vibrational energy.

2. The apparatus of claim 1 further comprising a focusing means to enhance said optical breakdown.

3. The apparatus of claim 1 wherein said second means for transmitting said acoustical vibrational energy further comprises an emulsification tip at the distal end of said surgical tip assembly.

4. The apparatus of claim 1 wherein said surgical tip assembly includes an irrigation channel for supplying irrigation fluid to said acoustic resonating chamber and an aspiration channel for supplying suction to said acoustic resonating chamber.

5. The apparatus of claim 3 wherein said emulsification tip further comprises at least one opening therethrough to permit said body tissue to enter said acoustic resonating chamber.

6. The apparatus of claim 1 wherein said surgical tip assembly is removably attachable to a handle adapted to be held by a surgeon and said second means for transmitting said acoustic vibrational energy is removably attachable to said surgical tip assembly.

7. The apparatus of claim 1 wherein said surgical tip assembly further comprises a hollow tube, said hollow tube housing said first means for transmitting said laser energy to achieve, optical breakdown with said laser energy and said second means for transmitting said acoustical vibrational energy to said body tissue.

8. The apparatus of claim 2 wherein said focusing means is selected from the group consisting of an optical sphere lens, a meniscus shaped lens, a fiber channel lens and a conical shaped lens.

9. A method of removing body tissue from a surgical site comprising the steps of:
   a) transmitting laser energy to an optical fiber;
   b) forming an acoustic resonating chamber by causing optical breakdown with said laser energy in material to generate acoustical vibrational energy;
   c) providing an emulsification tip spaced from and axially aligned with said acoustic resonating chamber to transmit said acoustical vibartional energy to said emulsification tip to induce vibratory motion therein; and
   d) contacting body tissue with said emulsification tip to initially emulsify a portion of said body tissue; and
   e) introducing body tissue initially emulsified in step (d) to said acoustic resonating chamber to further emulsify body tissue by said acoustical vibrational energy.

10. The method of claim 9 further comprising the step of supplying irrigating fluid to said acoustic resonating chamber.

11. The method of claim 9 further comprising the step of aspirating said body tissue in said acoustic resonating chamber.

12. The method of claim 9 further comprising the steps of
   i) supplying an irrigating fluid to said surgical site to enhance removal of said body tissue; and
   ii) removing said destroyed body tissue by aspiration.

13. The method of claim 9 further comprising the step of focusing said laser energy prior to step (b).

* * * * *